(12) United States Patent
Nagata

(10) Patent No.: US 8,546,134 B2
(45) Date of Patent: Oct. 1, 2013

(54) METHOD FOR ISOLATING NUCLEI

(75) Inventor: Takako Nagata, Washington, DC (US)

(73) Assignees: The George Washington University, Washington, DC (US); The United States of America as Represented by the Department of Veteran Affairs, Washington, DC (US)

( * ) Notice: Subject to any disclaimer, the term of this patent is extended or adjusted under 35 U.S.C. 154(b) by 244 days.

(21) Appl. No.: 12/960,688

(22) Filed: Dec. 6, 2010

(65) Prior Publication Data
US 2011/0136220 A1   Jun. 9, 2011

Related U.S. Application Data

(60) Provisional application No. 61/267,320, filed on Dec. 7, 2009.

(51) Int. Cl.
*C12N 1/00*   (2006.01)

(52) U.S. Cl.
USPC ........................................ 435/317.1; 435/820

(58) Field of Classification Search
USPC ...................... 435/317.1, 325, 820
See application file for complete search history.

(56) References Cited

PUBLICATIONS

Rickwood et al. Chapter 3. Isolation and characterization of nuclei and nuclear subfractions. Subcellular Fractionation: A Practical Approach, edited by Graham and Rickwood. Oxford University Press, 1997, reprinted 2002; p. 71-76.*
Nagata et al. Isolation of intact nuclei of high purity from mouse liver. Analytical Biochemistry 398 (2010) 178-184.*
K Bose et al., "An Improved Method of Preparing Nuclei for Absorption Cytophotometry", Journal of Histochemistry & Cytochemistry, 1985, pp. 65-68, vol. 33, No. 1.
K. Gorski et al., "Tissue-Specific in Vitro Transcription from the Mouse Albumin Promoter", Cell, Dec. 5, 1986, pp. 767-776, vol. 47.
Rachele Maggio et al., "Studies on Isolated Nuclei. Isolation and Chemical Characterization of Nuclear Fraction from Guinea Pig Liver" Journal of Cell Biology, Aug. 1963, pp. 267-291, vol. 18, No. 2.
W. C. Hymer et al., "Isolation of Nuclei from Mammalian Tissues Through the Use of Triton X-100", Journal of Histochemistry & Cytochemistry, 1964, pp. 359-363, vol. 12.
Günter Blobel et al., "Nuclei from Rat Liver: Isolation Method That Combines Purity with High Yield", Sciences, New Series, Dec. 30, 1966, pp. 1662-1665, vol. 154, No. 3757.
Yunn-Fang Ho et al., "Isolation of Liver Nuclei that Retain Functional Trans-membrane Transport", Journal of Pharmacological and Toxicological Methods, Nov. 1997, pp. 163-168, vol. 38, No. 3.
Dan Tapalaga et al., "NFKB and Caspase-3 Activity in Apoptotic Hepatocytes of Galactosamine-sensitized Mice Treated with TNFα", Journal of Histochemistry & Cytochemistry, 2002, pp. 1599-1609, vol. 50, No. 12.
A.N. Prusov et al., "Isolation of the Chromocenter Fraction from Mouse Liver Nuclei", Biochemistry, 2002, pp. 423-431, vol. 67, No. 4.
William D. Ball et al., "Two Independently Regulated Secretory Systems within the ACINI of the Submandibular Gland of the Perinatal Rat", The Journal of Cell Biology, 1984, pp. 112-122, vol. 33.
Edward S. Reynolds et al., "The Use of Lead Citrate at High pH as an Electron-Opaque Stain in Electron Microscopy", The Department of Anatomy, Harvard Medical School, Apr. 1, 1963, pp. 208-212.
Wayne Wray, Parallel Isolation Procedures for Metaphase Chromosomes Mitotic Apparatus, and Nuclei, 1975, pp. 75-89, vol. 40.

* cited by examiner

*Primary Examiner* — Taeyoon Kim
(74) *Attorney, Agent, or Firm* — Venable LLP; Nancy J. Axelrod; Henry J. Daley

(57) ABSTRACT

This invention relates to methods of isolating cell nuclei from the other cell components in cell samples, e.g., cell samples from cell cultures or tissue samples. The method does not comprise ultracentrifugation or super-centrifugation rather the method comprises centrifuging cell samples in a table-top conventional centrifuge or microfuge. The method also comprises the use of buffers that are substantially devoid of protease inhibitor or enzyme treatments. The methods facilitate separation of nuclei from nuclear outer membranes leaving the cellular structures and inner membranes of nuclei intact. The method also provides for rapid and consistent results.

29 Claims, 5 Drawing Sheets

METHOD FOR ISOLATING NUCLEI

This invention claims priority under 35 U.S.C. 119(e) to provisional application No. 61/267,320 filed Dec. 7, 2009, which is incorporated by reference in its entirety.

BACKGROUND OF THE INVENTION

Nuclear isolation is a common laboratory procedure which greatly facilitates the analysis of nucleotides, gene-protein interactions and other components and phenomena of cell nuclei. The principle of the method as developed in the mid-twentieth century consists of mechanical disruption of the cell membranes followed by separating the nuclei from cytoplasmic organelles and structures by sequential differential centrifugation in gradients of sucrose or other suitable media [Maggio et al., *J. Cell Biol.* 18 (1963) 267-291, Hymer & Kuff, *J. Histochem. Cytochem,* 12 (1964) 359-363]. Subsequently Blobel and Potter [Blobel & Potter, *Science,* 154 (1966) 1662-1665] modified the protocol of Maggio et al. [Maggio et al. 1963] with changes in the sucrose gradient density and utilization of a single 30 min centrifugation. These two protocols have been recognized and widely used as the standards for nuclear isolation. In the ensuing years, a number of variations have been employed to fit specific needs of particular tissues or nuclear components [Blobel & Potter (1966); Wray, *Methods Enzymol.* 40 (1975) 75-89; Bose & Allison, *J. Histochem. Cytochem.* 33 (1985) 65-68; Gorski et al., *Cell* 47 (1986) 767-776; Ho and Guenther, *J. Pharmacol. Toxicol. Methods* 38 (1997) 163-168; Tapalaga et al., *J. Histochem. Cytochem.* 50 (2002) 1599-1609, and; Prusov & Zatsepina, *Biochemistry* (Mosc) 67 (2002) 423-431] e.g., to preserve or remove the nuclear membranes, or adjust for the more difficult collection and disruption of cells from culture dishes or dense fibrous tissue. All the procedures introduced before the invention described herein produce samples containing nuclear outer membranes and damaged isolated nuclei. Although the method of Ho and Guenther [Ho and Guenther, (1997)] does not use high centrifugal force, it utilizes multiple homogenization steps with a rotary pestle, a 25,000×g centrifugal force step, requires the use of an ultracentrifuge rather than a table top centrifuge, takes 30 min longer total time than the methods of this invention and the isolated nuclei of Ho and Guenther are contaminated with cytoplasmic outer nuclear membrane.

BRIEF DESCRIPTION OF THE INVENTION

The methods described herein remove the nuclear outer membranes cleanly and produce isolated nuclei with their nuclear inner membranes intact. The removal of the outer nuclear membrane is a very desirable outcome, as the attached ribosomes otherwise would be a source of cytoplasmic RNA contamination [Blobel, and Potter, *Science,* 154 (1966) 1662-1665]. The methods of this invention are rapid, affordable, convenient and produce consistent reproducible results using a conventional table top centrifuge or microcentrifuge rather than an ultracentrifuge or a supercentrifuge for isolating nuclei from cells, particularly hepatocytes. Furthermore the methods comprise using buffers that are substantially devoid of protease inhibitors, such as e.g., aprotinin, leupetin, ethylene diamine tetraacetic acid ("EDTA"), and phenylmethyl sulfonylfluoride ("PMSF"), and using shorter centrifugation times and centrifugal forces than previously known methods for isolating nuclei.

This invention relates to a method(s) for isolation of nuclei from a cell sample, e.g., a sample comprising cells grown or maintained in cell culture, or cells from a tissue sample, e.g., a biopsy, e.g., a needle biopsy sample. The methods comprise (a) providing a sample of cells; (b) mechanically disrupting the cells in a buffer, e.g., mildly hypertonic buffer at an appropriate pH, e.g., about pH 7.4 to 7.6, to generate a disrupted cell sample; (c) centrifuging the disrupted cell sample at about 500-1000×g for about 5-15 minutes to pellet insoluble materials thereby forming a first supernatant and a first crude nuclei pellet; (d) separating the first supernatant from the first crude nuclei pellet; (e) resuspending the pellet is an appropriate buffer, e.g., a highly hypertonic buffer, at an appropriate pH, e.g., about pH 7.4-7.6; (f) centrifuging the resuspended pellet of (e) at about 12,000-30,000×g for about 10-60 minutes to generate a second nuclei pellet and a second supernatant; and then (g) separating the second supernatant and isolated pellet of (f), wherein the isolated nuclei pellet contains purified nuclei. In one aspect of this invention the second nuclei pellet is frozen at about −60 to −80° C., which may be resuspended in an appropriate buffer, e.g., a hypertonic buffer. The nuclei pellet may also be resuspended in such buffer prior to freezing or the pellet may be frozen and then thawed under appropriate conditions suitable for maintaining the integrity of the isolated nuclei and then resuspended.

In a particular aspect, this invention relates to a method for isolation of nuclei comprising: (a) providing a sample of cells; (b) mechanically disrupting the cellular membrane of the cells in ice-cold buffer comprising mildly hypertonic medium pH 7.4-7.6 to generate a disrupted cell sample; (c) centrifuging the disrupted cell sample at about 600×g for 10 minutes at 4° C. in a microcentrifuge to generate a first supernatant and a first crude nuclei pellet; (d) separating the first supernatant from the first pellet; (e) resuspending the first crude nuclei pellet in ice-cold mildly hypertonic buffer pH 7.4-7.6; (f) washing the first crude nuclei pellet by centrifuging the resuspended pellet at about 600×g for about 10 minutes at 4° C. in a microcentrifuge to generate a second supernatant and a second crude nuclei pellet; (g) separating the second supernatant from the second crude nuclei pellet; (h) resuspending the second crude nuclei pellet is ice-cold highly hypertonic buffer pH 7.4-7.6; (i) centrifuging the resuspended pellet of (g) at about 16,000×g at 4° C. for 30 minutes in a microcentrifuge to generate a nuclei pellet and a third supernatant; (j) separating the third supernatant and nuclei pellet of (i); (k) resuspending the nuclei pellet of (i) in ice-cold mildly hypertonic buffer pH 7.4-7.6; (l) centrifuging the resuspended pellet of (k) at 600×g for 10 minutes at 4° C. in a microcentrifuge to generate a supernatant and a washed nuclei pellet; (m) separating the supernatant and washed nuclei pellet of (l) and resuspending the washed nuclei pellet of (i) in ice-cold mildly hypertonic buffer pH7.4-7.6. In one aspect of this invention the washed nuclei pellet is frozen at about −60 to −80° C. The washed nuclei pellet may be resuspended in an appropriate buffer, e.g., a hypertonic buffer, prior to freezing or the pellet may be frozen and then thawed under appropriate conditions suitable for maintaining the integrity of the isolated nuclei.

DETAILED DESCRIPTION OF THE INVENTION

Figure 1:
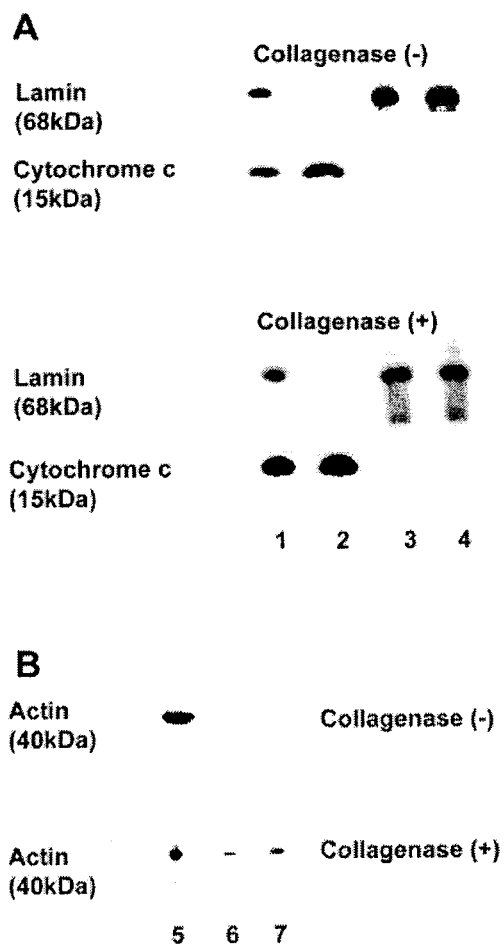
FIG. 1. Western blotting with Lamin B1 and Cytochrome C (A) and Actin(B). (A) Lanes are: 1, Cell Suspension; 2, Cytoplasmic Portion; 3, Nuclei isolated with moderate centrifugal force (MCF, 16,000×g); 4, Nuclei isolated with high centrifugal force (HCF, 70,000×g). Upper panel: without collagenase [collagenase (−)]. Lower panel: with collagenase [collagenase (+)]. (B) Lanes are: 5, Crude Nuclei; 6, Nuclei isolated with moderate centrifugal force; 7, Nuclei isolated with high centrifugal force.

The methods of this invention are rapid and convenient methods for isolating nuclei and all the centrifugation steps of the invention can be executed in a single tube. The methods comprise centrifuging a sample of disrupted cells containing nuclei in a conventional table top centrifuge or microcentrifuge rather than in an ultracentrifuge or a supercentrifuge to generate a crude nuclei sample. The crude nuclei-containing sample is then further purified also using a conventional table top centrifuge or microcentrifuge rather than in an ultracentrifuge or a supercentrifuge. In addition, the methods comprise using buffers that are substantially devoid of protease inhibitors, such as, e.g., aprotinin, leupetin, EDTA, and PMSF. The centrifugation times and centrifugal forces and the amounts of starting materials that are used in the methods of this invention are far less than those needed in previously known methods for isolating functional cell nuclei of sufficient quality, e.g., substantially devoid of contaminating cytoplasmic RNA and mitochondrial DNA, and sufficient quantity that suitable for assays of nuclear activities. Such assays include, e.g., assays of nuclear membrane transport, e.g., transport of a transcription factor(s) without the need to employ complicated gel shift assays, accurate analysis of autosomal genotyping wherein the contamination of mitochondrial DNA must be strictly avoided and assays for identifying newly transcribed RNA in isolated nuclei.

The nuclei-containing disrupted cell sample may be prepared by any method known in the art for disrupting the outer cellular membrane while not disrupting the nuclear membrane. Preferably the method comprises mechanically disrupting cells. The cells may be disrupted by shearing the cells such that the outer membrane of the cells is disrupted but the nuclei are left substantially intact. For example, the cells may be forced through a cell strainer with 40 µm pore size (e.g., a 3D Falcon cell strainer, Fisher Scientific, Suwannee, Ga.) that is affixed to a syringe, e.g., a 3 ml Kendall Monoject syringe (Tyco Healthcare Group LP, Mansfield, Mass.). In one embodiment, disrupted cells are obtained from a tissue sample, e.g., the tissue sample is cut into pieces and a single cell suspension of cells from the tissue sample is obtained by any method known in the art and the cells disrupted by shearing as described above.

The disrupted cell sample is centrifuged in the cold, e.g., 4° C., at about 500-1000×g for about 5-15 minutes, preferably about 10 minutes, to pellet insoluble materials thereby forming a first supernatant and a first crude nuclei pellet. Preferably the disrupted cell sample is centrifuged at 500-700×g, more preferably, the disrupted cell sample is centrifuged at 600×g.

The crude nuclei pellet is resuspended in a mildly hypertonic buffer having a pH of about 7.2 to about 7.6, preferably about pH 7.4 to 7.6. A "mildly hypertonic buffer" comprises for example about 250 mM sucrose, For example the mildly hypertonic buffer may be a buffer comprising 250 mM sucrose, 1 mM to 5 mM $MgCl_2$, preferably about 5 mM $MgCl_2$, and about 10 mM Tris-HCL pH7.4-7.6, preferably about 10 mM Tris-HCL pH7.4-7.6, or may be a buffer comprising 250 mM sucrose and PBS (calcium-free or calcium and magnesium-free PBS) pH 7.4. The mildly hypertonic medium may consist essentially of 250 mM sucrose, 5 mM $MgCl_2$, 10 mM Tris-HCL pH7.4 or may consist essentially of 250 mM sucrose in PBS (calcium and magnesium-free) pH7.4.

Optionally, the crude nuclei pellet may be washed by resuspending the pellet in the mildly hypertonic solution and repeating the centrifugation step applied to the disrupted cell sample.

The highly hypertonic buffer functions as a cushion and gives the best condition to cells for separating nuclei from the other cell components and protects their integrity and structures including nuclear inner membranes. A highly hypertonic buffer may be e.g., a Tris-HCl buffer or a phosphate buffered saline at pH 7.2 to 7.6, preferably about pH 7.4 and comprises about 1.8 to about 2.2M sucrose, preferably about 2.0-about 2.2 M sucrose. The buffer may further comprise about 0.1 mM to about 5 mM, preferably about 1 mM, $MgCl_2$. In one aspect of this invention the highly hypertonic buffer comprises about 2.0M sucrose, in a Tris-HCl buffer, e.g., 1 mM $MgCl_2$ and 10 mM Tris-HCl pH 7.4, or comprises 2.0M sucrose in PBS (calcium-free or calcium and magnesium-free PBS), pH 7.4. Preferably the highly hypertonic buffer consists essentially of 2.0M sucrose, 1 mM $MgCl_2$ and 10 mM Tris-HCl, pH 7.4 or consists essentially of 2.0M sucrose in calcium and magnesium-free PBS, pH 7.4.

Preferably the buffers useful in this invention are substantially devoid of protease inhibitors. For example, the buffers comprise less than 5 mM PMSF, less than about 10 mM EDTA, less than about 20 ug/ml aprotinin and/or less than about 20 ug/ml leupeptin. Preferably the buffers comprise less than about 1 mM PMSF, less than about 5 mM EDTA, less than about 10 ug/ml aprotinin and/or less than about 10 ug/ml leupeptin. More preferably the buffers comprise less than about 0.5 mM PMSF, less than about 2.5 mM EDTA, less than about 5 ug/ml aprotinin and/or less than about 5 ug/ml leupeptin. Most preferably the buffers do not contain protease inhibitors.

The resuspended crude nuclei pellet is centrifuged at 12,000-20,000×g, preferably at about 14,000-16,000×g and more preferably at about 16,000×g, for a time sufficient to generate a second nuclei pellet substantially free of contaminating cytoplasmic RNA and mitochondrial DNA. For example, the resuspended crude nuclei pellet may be centrifuged for at least 10 minutes, e.g., about 10 to about 60 minutes, preferably about 10 to about 30 minutes, in the cold, e.g., at about 4° C. The resuspended crude nuclei pellet is centrifuged in a convention table top centrifuge or microfuge. Such table top centrifuges or microfuges are commercially available from e.g., Beckman Instruments, Palo Alto, Calif.).

An advantage of the invention is that the cell samples may all be centrifuged in a single tube, a conical microcentrifuge tube, and in a conventional table top centrifuge or a microcentrifuge rather than an ultracentrifuge or supercentrifuge. Conventional table top centrifuges or microcentrifuges are typically designed to accommodate centrifuge tubes having a volume of 2.2 ml or less, typically 200 ul to 2 ml, commonly 1.5 ml. This aspect of the invention contributes to the ease and convenience of the disclosed methods. Furthermore, small samples can be used in the methods. For example, the disrupted cell sample may be in a volume of about 100 ul to about 2 ml, preferably about 500 ul to 1.5 ml.

Another advantage of this invention is that the method does not require layering the crude nuclei pellet resuspended in hypertonic buffer over another more highly hypertonic buffer to obtain the isolated nuclei substantially free of contaminating cytoplasmic RNA and mitochondrial DNA.

Still another advantage of this invention is that the recovery of intact nuclei substantially free of cytoplasmic RNA and mitochondrial DNA is more efficient than previously described methods and thus very small samples of cells are sufficient to provide nuclei of a quality and quantity that is suitable for assays of nuclear activities. Such assays include but are not limited to, e.g., assays of nuclear membrane transport, e.g., transport of a transcription factor(s) without the need to employ complicated gel shift assays, accurate analysis of autosomal genotyping wherein the contamination of mitochondrial DNA must be strictly avoided and assays for identifying newly transcribed RNA in isolated nuclei. The cell sample may be a sample of cells from cell culture or may be cells from a tissue sample and may be less than about 10 g, less than about 5 g or less than about 2.5 grams. Sufficient amounts of nuclei may be recovered from about 0.1 to about 10 g of cells or tissue. The tissue sample may be a biopsy, e.g., a needle biopsy sample.

Nuclei substantially free of cytoplasmic RNA means that greater than 99% of the cytoplasmic RNA of the original sample has been removed. Nuclei substantially free of mitochondrial DNA means that at least 99% of the mitochondrial DNA of the original sample has been removed.

The cells may be a mammalian, avian or amphibian cells. The mammalian cells may be, e.g., murine, porcine, bovine, equine or primate cells.

The cells may also be obtained from cell culture or a tissue sample. The tissue sample may be, e.g., a tissue sample from a normal or diseased tissue. The tissue may be, e.g., a liver, heart, spleen, muscle, or lung tissue.

Another embodiment of the method of this invention consists essentially of (a) providing a sample of cells; (b) mechanically disrupting the cells in a buffer, e.g., a mildly hypertonic buffer at about pH 7.4, to generate a disrupted cell sample; (c) centrifuging the disrupted cell sample at about 600×g for about 10 minutes to pellet insoluble materials thereby forming a first supernatant and a first crude nuclei pellet; (d) separating the first supernatant from the first crude nuclei pellet; (e) resuspending the pellet is a highly hypertonic buffer, at an appropriate about pH 7.4; (f) centrifuging the resuspended pellet of (e) at about 16,000×g for about 30 minutes to generate a second nuclei pellet and a second supernatant; and then (g) separating the second supernatant and isolated pellet of (f), wherein the isolated nuclei pellet contains purified nuclei.

A further embodiment of the method of this invention for isolation of nuclei comprises:

(a) providing a sample of cells;

(b) mechanically disrupting the cellular membrane of the cells in ice-cold mildly hypertonic buffer pH 7.4-7.6 to generate a disrupted cell sample;

(c) centrifuging the disrupted cell sample at 600×g for 10 minutes at 4° C. in a microcentrifuge to generate a first supernatant and a first crude nuclei pellet;

(d) separating the first supernatant from the first pellet (e) resuspending the first crude nuclei pellet in ice-cold mildly hypertonic buffer pH 7.4-7.6, (f) washing the first crude nuclei pellet by centrifuging the resuspended pellet at 600×g for 10 minutes at 4° C. in a microcentrifuge to generate a second supernatant and a second crude nuclei pellet;

(g) separating the second supernatant from the second crude nuclei pellet;

(h) resuspending the second crude nuclei pellet is ice-cold highly hypertonic buffer pH 7.4-7.6;

(i) centrifuging the resuspended pellet of (g) at 16,000×g at 4° C. for 30 minutes in a microcentrifuge to generate a nuclei pellet and a third supernatant;

(j) separating the third supernatant and nuclei pellet of (i);

(k) resuspending the nuclei pellet of (i) in ice-cold mildly hypertonic buffer pH 7.4-7.6;

(l) centrifuging the resuspended pellet of (k) at 600×g for 10 minutes at 4° C. in a microcentrifuge to generate a supernatant and a washed nuclei pellet.

(m) separating the supernatant and pellet of (l) and resuspending the nuclei pellet of (i) in ice-cold mildly hypertonic buffer pH7.4-7.6.

1. In another embodiment, the method of this invention consists essentially of the foregoing steps (a) through (m). In still another aspect of this invention the method consists of the foregoing steps (a) through (m). Optionally the pellet of (m) is frozen at −60° C. to −80° C. rather than resuspended.

EXAMPLES

Example 1

Step 1. Each sample from animal tissues was minced and about 0.5 g was mashed through a 3D Falcon cell strainer with 40 μm pore size (Fisher Scientific, Suwannee, Ga.) with the plunger from a 3 ml Kendall Monoject syringe (Tyco Healthcare Group LP, Mansfield, Mass.) into a plastic Petri dish (Fisher cat. no. 08-771-1) on ice with 4 ml of a ice-cold mildly hypertonic buffer, buffer A (250 mM sucrose, 5 mM $MgCl_2$, 10 mM Tris-HCl at pH 7.4), per 0.5 g of the sample.

Step 2. The mass of disrupted cells was centrifuged at 600×g for 10 mM at 4° C. in conical microtubes of 1.5 ml (1 ml of the suspension/tube) in a table top microcentrifuge. The supernatant (cytoplasmic portion) was removed and stored at −70° C. for further analysis.

Step 3. The pellet was gently resuspended in 1.4 ml of ice-cold buffer A and centrifuged as in step 2. The supernatant was discarded.

Step 4. This second crude nuclei pellet was resuspended in 9 volumes of a ice-cold highly hypertonic buffer B (2.0 M sucrose, 1 mM $MgCl_2$, 10 mM Tris-HCl, pH 7.4), well-mixed, and centrifuged in conical microcentrifuge tubes at 16,000×g at 4° C. for 30 min in a table-top centrifuge.

The crude nuclei separated into two layers. The upper layer, which was brownish and sticky, was deposited at the surface of the buffer while a white pellet of isolated nuclei was on the bottom of the tube. The tube was inverted and pushed gently against a paper towel, removing most of the upper layer by absorption onto the towel. Materials adhering to the tube walls were wiped off with cotton swabs.

Step 5. The pellet of isolated nuclei is washed in ice-cold buffer A once by resuspending the pellet and then centrifuging the resuspended pellet at 600×g in a microcentrifuge at 4° C. for 5 minutes. The washed pellet was then kept at −70° C. for further analysis.

Example 2

Mouse liver: mice were anesthetized by inhalation of ca. 2% isoflurane (Abbott Animal Health, Abbott Park, Ill.). The abdomen is cut open by midline incision and the Inferior vena cava and portal vein were exposed. To remove blood from the liver, heparin (10,000 USP units/ml, Baxter Healthservices; 150 ul in 200 ul of [calcium and magnesium-free] PBS) was manually injected through the Inferior vena cava with a 1 ml syringe and 25-gauge-one-inch (monoject 250) needle (Becton Dickinson, Franklin Lakes, N.J.) followed by cutting the portal vein. Subsequently, 15 ml of ice-cold PBS is injected through the same needle with a B-D 20 ml syringe (Becton Dickinson) at the speed of 3 ml/min. The liver was excised, cleaned of extraneous tissues, and weighed. The entire liver was processed according to the procedures mentioned above.

Human Liver: liver tissues obtained by needle biopsy or dissection were placed in ice-cold PBS and weighed. The samples were processed according to the procedures mentioned above.

Example 3

Animals: Specific pathogen-free C57BL/6 mice (9-12 weeks old) were obtained from Jackson Laboratories, Bar Harbor, Me. They were housed under pathogen-free conditions in the Washington, D.C., Veterans Affairs Medical Center Animal Care Facility with a light/dark cycle of 12 h each and water and a commercial pelleted diet available ad libitum. This research was conducted under an Institutional Animal Care and Use Committee-approved protocol.

Isolation Procedure

Four variations in nuclear isolation procedures were compared: Cell collection and disruption (steps 1 and 2) was accomplished with and without in vivo collagenase perfusion, and the isolated nuclear pellet (step 7) was obtained by moderate (16,000×g) vs. high (70,000×g) centrifugal force (MCF and HCF, respectively). These were performed independently for four runs.

Step 1. Mice were anesthetized by inhalation of ca. 2% Isoflurane (Abbott Animal Health, Abbott Park, Ill.). The abdomen was cut open by midline incision and the inferior vena cava and portal vein were exposed. To remove blood from the liver, heparin (10,000 USP units/ml) 150 ul in 200 ul of calcium and magnesium-free PBS) was manually injected through the inferior vena cava with a 1 ml syringe and 25-gauge-one-inch (monoject 250) needle (Becton Dickinson, Franklin Lakes, N.J.) followed by cutting the portal vein. Subsequently, 15 ml of ice-cold PBS was injected through the same needle with a B-D 20 ml syringe (Becton Dickinson) at the speed of 3 ml/min. The liver was excised, cleaned of extraneous tissues, and weighed.

Step 2. The entire liver was mashed gently through a 3D Falcon cell strainer with 40 μm pore size (Fisher Scientific, Suwannee, Ga.) with the plunger from a 3 ml Kendall Monoject syringe (Tyco Healthcare Group LP, Mansfiled, Mass.) into a plastic Petri dish (Fisher cat. no. 08-771-1) with 4 ml of ice-cold buffer A (250 mM sucrose, 5 mM $MgCl2$, 10 mM Tris-HCl, pH 7.4) per 0.5 g of the liver forming a disrupted cell sample.

Step 3. The mass of disrupted cells was centrifuged at 600×g for 10 min at 4° C. in an IEC6P8R centrifuge (International Equipment Co, Needham, Mass.). The supernatant (cytoplasmic portion) was removed and kept at −70° C. for further analysis.

Step 4. The pellet was gently resuspended in 1.4 ml of ice-cold buffer A and centrifuged as in step 3. The supernatant was discarded.

Step 5. This crude nuclei pellet was resuspended in 9 volumes of ice-cold buffer B (2.0 M sucrose, 1 mM $MgCl2$, 10 mM Tris-HCl, pH 7.4), well-mixed, distributed to microtubes of 1.5 ml, and centrifuged at 16,000×g at 4° C. for 30 min in an Eppendorf 5415C centrifuge (Brinkman Instruments, Westbury, N.Y.), or at 70,000×g at 4° C. for 80 min in a Beckman L8-70M ultracentrifuge (Beckman Instruments, Palo Alto, Calif.).

Step 6. The crude nuclei were separated into two layers. The upper layer, which was brownish and sticky, was deposited at the surface of the buffer while the white pellet of isolated nuclei was on the bottom of the tube. The tube was inverted and pushed gently against a paper towel, removing most of the upper layer by absorption onto the towel. Materials adhering to the tube walls were wiped off with cotton swabs.

Step 7. The pellet of isolated nuclei was resuspended in ice-cold buffer A and kept at −70° C. for further analysis.

Isolation with Collagenase

In step 1, collagenase IV (Sigma-Aldrich, Milwaukee, Wis.) was added to the 15 ml of PBS at 10 mg/ml at 37° C. The rest of the procedures were exactly the same as listed above.

Western Blotting

Crude nuclei and isolated nuclei were suspended in boiled lysis buffer (1% SDS, 10 mM Tris-HCL at pH 8.5, 5 mM $MgCl2$, and 1 mM orthvanadium) and boiled for 5 min. They were centrifuged at 16,000×g at 4° C. for 20 min in the Eppendorf centrifuge. The pellets were collected and the protein concentration was colorometrically measured with bovine serum albumin standard (Bio-Rad, Hercules, Calif.) and RC DC protein assay (Bio-Rad) by SpectraMax 190 (Molecular Devices, Downingtown, Pa.). The same amount of protein was loaded for each sample on 4-15% gradient gels (Bio-Rad) along with molecular markers (Bio-Rad) in running buffer (0.1% SDS in Tris/Glycine Buffer (Bio-rad)) under 90 constant volts at 4° C. The proteins in the gels were transferred onto PVDF membrane (Bio-Rad) in transfer buffer (20% EtOH in Tris/Glycine Buffer (Bio-rad)) under 40 constant volts for one hour at 4° C. The membranes were blocked overnight in blocking buffer (5% non-fat milk (Bio-Rad) in PBS) at 4° C. They were washed four times in washing buffer (0.05% TWEEN™-20 in PBS), and reacted with primary antibodies overnight at 4° C. as follows: anti-lamin B1 (Abcam, Cambridge, Mass.) was diluted at 1:1000; anti-cytochrome c (BD Pharmingen, San Jose, Calif.) was diluted at 2 ug/ml in PBS with 0.5% bovine serum albumin ("BSA"); and HRP-conjugated actin (C-2) (Santa-Cruz, Santa Cruz, Calif.) was diluted at 1:2000 in PBS with 2.5% non-fat milk. They were washed four times in washing buffer and stained with secondary antibodies diluted in washing buffer (1:1000 HRP conjugated goat-anti rabbit IgG for anti-lamin B1 and goat-anti mouse IgG for anti-cytochrome c from Santa-Cruz) for 1 hr. After washing four times, they were developed in ECL solution (Perkin-Elmer, Waltham, Mass.) for 1 min and the fluorescence was measured and photographed by Fluoro-Chem 8800 (Alpha Innotech Corporation, San Leandro, Calif.).

RNA Purification

Total RNA was purified from the isolated nuclei according to the manufacturer's instruction using RNA-Stat from Iso-Tex Diagnostics (Friendswood, Tex.), and quantified by SpectraMax 190 (Molecular Devices).

Morphology

At least two samples were obtained from different runs or portions of runs that were split for biochemical and morphologic analyses and run in parallel. In order to maintain the original stratification of the pellets, they were fixed in situ in the centrifuge tubes. A pilot study in which the pellets were fixed in formaldehyde and embedded in paraffin failed in this objective, as during removal from the centrifuge tubes, the larger pellets were often distorted and many of the small ones were lost. Thus, it was necessary to embed them in a harder substance. Except as noted, all of the following were performed at ambient temperature. Pellets were fixed for 6 to 8 hours in 4.0% glutaraldehyde (Electron Microscopy Sciences, Fort Washington, Pa.; EMS) in 0.1M $Na_2HPO_4$ and 0.001M $CaCl_2$, pH 7.4, washed in the phosphate buffer, then in 0.1M sym-Collidine (2,4,6-trimethlypyridine; EMS), pH 7.4. They then were post-fixed for two hours in 1.0% $OSO_4$ (EMS) in the sym-Collidine buffer, washed in the sym-Collidine buffer, and dehydrated via ethanol and propylene oxide (EMS). Embedding was a two stage process. The pellet was immersed in 0.3 ml of a 1:1 (v/v) mixture of epon (EMbed 812; EMS) and propylene oxide, and after the propylene oxide had evaporated overnight, the remaining epon was hardened at 60° C. for 48 hours. Each centrifuge tube then was cut open and the embedded pellet was divided into two or more pieces to fit into the tips of BEEM® capsules (EMS). The capsules were filled with additional epon, which then was hardened as before. The amount of cell suspension used in the parallel runs for morphologic samples was small enough to result in nuclear pellets being thin (0.5 mm) disks, which allowed for rapid and thorough penetration of fixatives, washes, dehydration solvents, and epon. The process facilitated both good preservation and orientation of the pellet for sectioning at 1.0 μm on a Reichert-Jung Ultracut E ultramicrotome (Leica Microsystems, Bannockburn, Ill.).

For light microscopy, sections were mounted on SUPER-FROST®/plus glass slides (Fisher Scientific), stained either with azur II/methylene blue [Richardson et al. Stain Technol 35 (1960) 313-23 incorporated herein by reference] or basic fuchsin/toluidine blue [Ball and Redman, Eur J Cell Biol 33 (1984) 112-22, incorporated herein by reference], and coverslips were mounted with PRO-TEXX™ medium (American Scientific Products, McGraw Park, Ill.). For tissue localization of actin, cytochrome c and lamin B1, a portion of a mouse liver was fixed for 6 hr in sodium phosphate-buffered formalin, processed through graded solvents and embedded in paraffin. Sections were cut at 8 μm and mounted on SUPER-FROST®/plus glass slides. Primary antibodies were the same as were used for the Western blots. Samples were subjected to Immunohistochemistry (IHC) with and without antigen retrieval in Reveal buffer in a pressure cooker, using Envision and dual link HRP in a Dako (Carpenteria, Calif.) autostainer, and counterstained with hematoxylin. The chromogen was 3,3-diaminobenzidine (DAB). Formaldehyde and DAB were purchased from Government Scientific Solutions, Alexandria, Va. Dyes were obtained as follows: azur II (lot # 880311), EMS; basic fuchsin (760154) and toluidine blue O (766486), Fisher Scientific; and methylene blue (1343P), Allied Chemical, Morristown, N.J. Sections were viewed on an Olympus BX41 microscope with planapochromatic optics (Olympus America, Center Valley, Pa.) and photographed with an Olympus Q-Colors digital camera attachment with software for an iMAC ZOCX computer (Apple, Cupertino, Calif.).

For transmission electron microscopy (TEM), sections were cut at ca. 70 nm, mounted on 200 mesh copper grids (EMS) and stained with uranyl acetate [Reynolds, J Cell Biol 17 (1963) 208-12, incorporated herein by reference] and lead citrate [Watson, J Biophys Biochem Cytol 4 (1958) 727-30, incorporated herein by reference]. These were viewed and photographed with a JEOL model JEM 100CX electron microscope. Prints were converted to digital images with an HP Scanjet 4890 scanner (Hewlett-Packard, Hershey, Pa.), and collated into panels and labeled using Adobe Photoshop CS3 software (Adobe Systems, San Jose, Calif.).

Analyses

The data acquired by SpectraMax190 were analyzed by SoftMaxPro (Molecular Devices, Sunnyvale, Calif.). The data acquired by Fluoro-Chem 8800 were analyzed by ALPHAVIEW™ (Alpha Innotech Corporation) and ADOBE® PHOTOSHOP® (Adobe Systems Incorporated, San Jose, Calif.).

Results

Biochemical Evaluation

As demonstrated in the upper panel of FIG. 1(A), which is a part of this application, without collagenase treatment, virtually intact and pure nuclei were obtained; i.e., the cytochrome c staining indicated that there were no cytoplasmic and membranous contaminations in the isolated nuclei, while the lamin B1 bands were single and thicker in the isolated nuclei and absent in the cytoplasmic portion. In the lower panel of FIG. 1(A) with collagenase treatment, the isolated nuclei showed multiple bands and smears in lamin B1. As shown in FIG. 1(B), without collagenase treatment, actin was barely detected in the isolated nuclei, whereas with collagenase treatment, definite bands were associated with the isolated nuclei. These bands were weaker than that in the crude nuclei, and were thicker with HCF than with MCF.

As shown in Table 1, the yield (number of nuclei) was 10-fold higher with collagenase than without collagenase. The purity was more than 95% except for the samples using both HCF and collagenase. Total RNA was higher with HCF than with MCF, and higher with collagenase than without collagenase.

TABLE 1

Analysis of Isolated Nuclei

| Collagenase | Centrifugal Force | Nuclei Number/g | Purity (%) | RNA (ug) |
|---|---|---|---|---|
| No | Moderate | $22 \times 10^6$ | 98.3 | 9.0 |
| No | High | $18 \times 10^6$ | 96.0 | 11.2 |
| With | Moderate | $26 \times 10^7$ | 100 | 18.7 |
| With | High | $17 \times 10^7$ | 91.3 | 23.6 |

Figure 2:
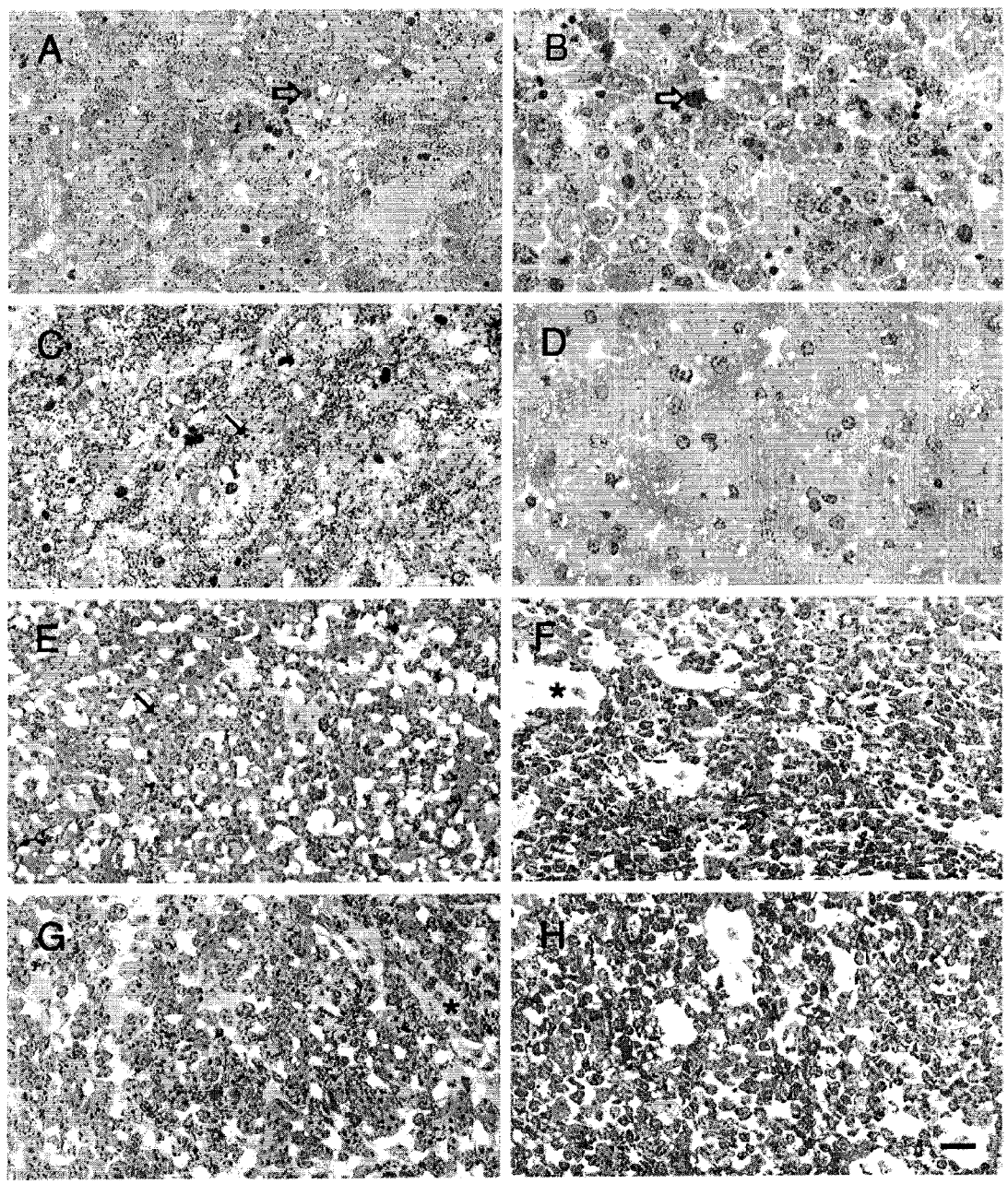
FIG. 2. Photomicrographs of semi-thin epon sections of pellets collected at representative steps in the preparation of samples of mouse hepatocyte nuclei by differential centrifugation. Cell suspensions of mouse liver were prepared without (A, C, E, and G) and with (B, D, F, and H) collagenase digestion. (A and B) cell suspensions; (C and D) crude nuclei; Isolated nuclei prepared with moderate (E and F) and high (G and H) centrifugal force. Empty arrows=erythrocytes, solid arrows=nucleoli, asterisks=pools of cellular debris. A and D-H, azur II/methylene blue stain; B and C, basic fuchsin/toluidine blue O stain. All are approximately the same magnification; bar=50 µm.
Figure 3:
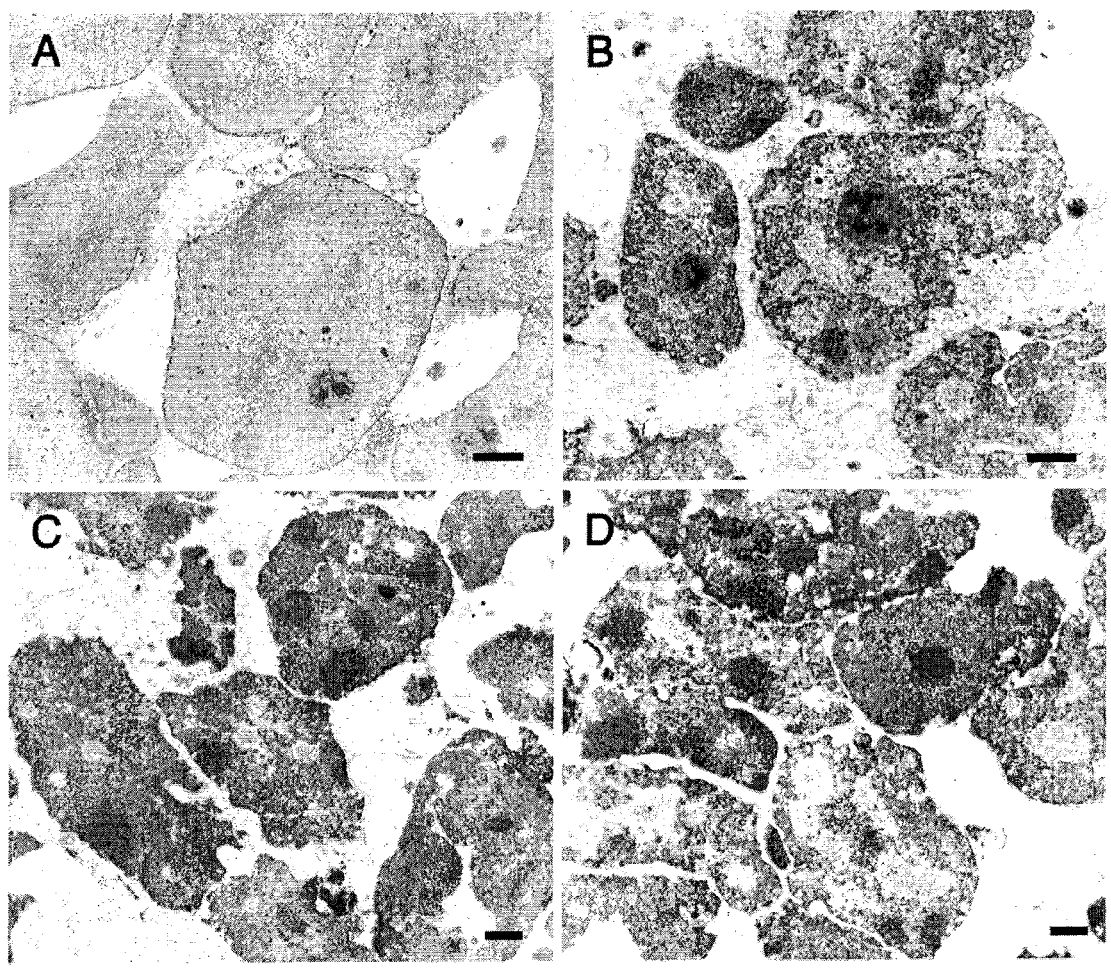
FIG. 3. Transmission electron micrographs of the isolated nuclei. Nuclear preparation was without (A and C) or with (B and D) collagenase digestion, and with moderate (A and B) or high (C and D) centrifugal force. The nuclei in A have the smoothest borders and are more homogeneous, and there are fewer segments of broken nuclear membrane in A and B than in C and D. Magnification bars=1 µm.

Nuclei were counted under microscope at 100× using trypan blue staining. Purity was calculated as the number of nuclei/total number of objects including nuclei and cells, virtually all of which were hepatocytes. The liver cells were well-separated from each other immediately after treatment with collagenase (data not shown). The RNA content of the pure nuclei is represented by the following lowest-to-highest hierarchy: No collagenase, MCF>No collagenase, HCF>collagenase, MCF>collagenase, HCF.Morphologic evaluation Representative photomicrographs of semi-thin epon sections of the cell suspension, crude nuclei and isolated mouse liver nuclei are presented in FIG. 2. Transmission electron micrographs of the isolated nuclei are shown in FIG. 3, which is a part of this application. In general, the cell suspensions consisted of masses of almost all hepatocytes while the isolated nuclear pellets consisted of highly concentrated nuclei, regardless of the choice of centrifugal force or whether or not collagenase was used in separating the cells. In addition, the majority of nuclei had distinct membranes and multiple prominent nucleoli in the cell suspension and crude nuclear samples regardless of the use or omission of collagenase. The isolated nuclei prepared without collagenase also retained these characteristics (FIGS. 2 E and G, and 3 A and C,), with the shape and membrane integrity being better with MCF than with HCF. Almost all of the isolated nuclei prepared by any of the four variations had no outer nuclear membrane but had retained the inner membrane. However, the isolated nuclei that had been prepared with collagenase in the initial step had fewer and smaller nucleoli and more segments of indistinct or torn membranes (FIGS. 2 F and H and 3 B and D).

Morphologically, the condition of the isolated nuclei thus is represented by the following best-to-worst hierarchy: no collagenase, MCF>no collagenase, HCF>collagenase, MCF>collagenase, HCF.

Figure 4:
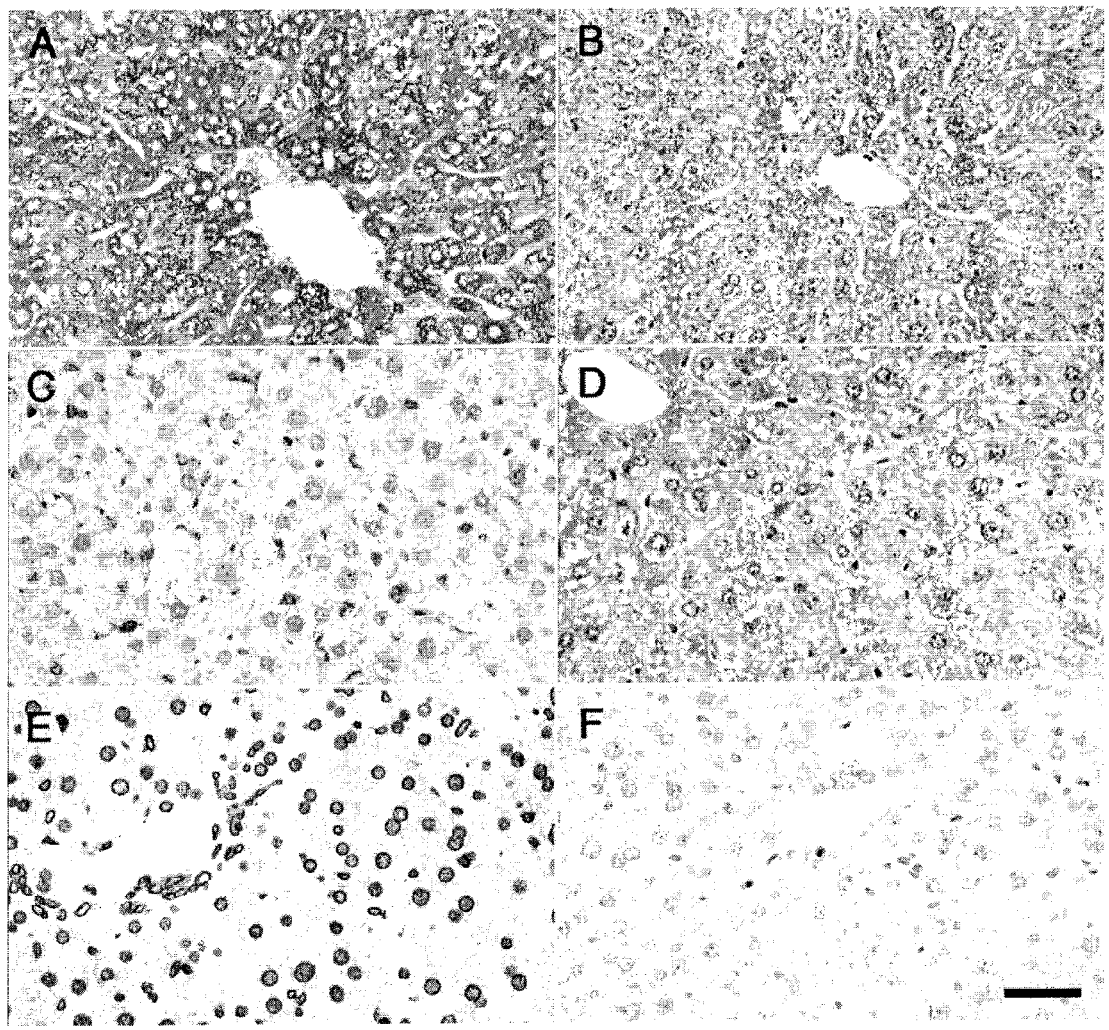
FIG. 4. Immunohistochemical localization in mouse liver of antibodies used in the Western blots. A and B, anti-cytochrome c; C and D, anti-actin; E, anti-lamin B1; and F, no primary antibody (negative control). Antigen retrieval was used on sections in A, C, E and F; not in B and D. DAB-H202 chromogen reactions (brown precipitate) and hematoxylin counterstain. Magnification bar=50 µm.
Figure 5:
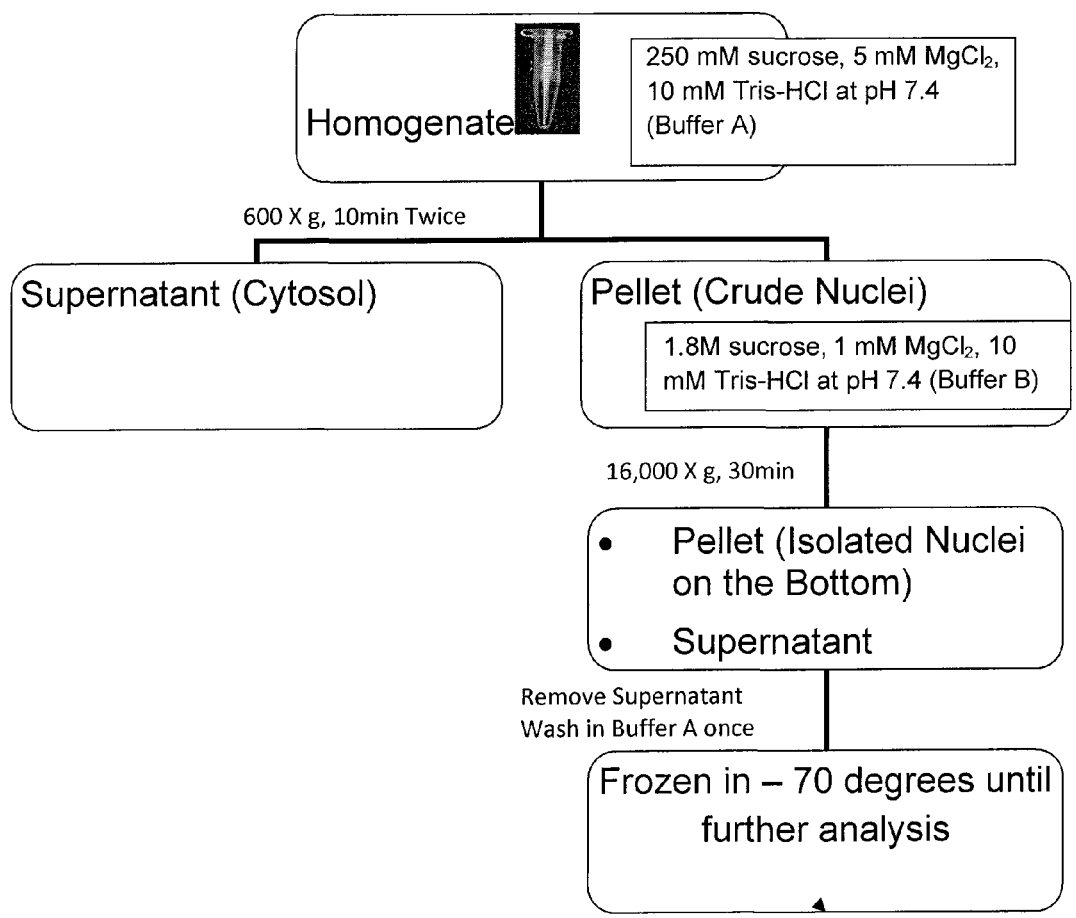
FIG. 5 depicts a schematic representation of an embodiment of the methods described herein.

The IHC results are portrayed in FIG. 4. Cytochrome c localized exclusively to the cytoplasm both with (4A) and without (4B) antigen retrieval. With antigen retrieval (4C), actin antibodies localized heavily to the cytoplasm, presumably to smooth muscle actin, and overlapped the periphery of the nuclei of cells around blood vessels. The cytoplasm and nuclei of hepatocytes reacted weakly and not at all, respectively. Without prior antigen retrieval (4D), there were moderate to strong reactions to the actin antibodies throughout the cytoplasm and within the peripheral portions of the nuclei of all cells. Lamin B1 antibodies (4E) reacted exclusively in the nuclei of all cell types, often with a darker rim. No DAB reaction occurred when the primary antibodies were omitted (4F).

The results presented herein demonstrate that the methods of this invention comprising MCF without prior in vivo collagenase treatment produced nuclei that were surprisingly superior morphologically and of higher purity in terms of total RNA than the nuclei produced by other methods using collagenase or HCF. The crude nuclei obtained with methods comprising an in vivo collagenase perfusion step had larger and more numerous cell clusters than those derived without collagenase (data not shown). The larger amount of cells in the original cell suspension resulted in a higher yield of isolated nuclei. However, collagenase perfusion increased the RNA and actin contamination of the isolated nuclei and these were further increased by HCF. In addition, the use of collagenase resulted in lamin degradation.

The morphologic results correlated well with the biochemical data. Ultrastructural analysis demonstrated that the nuclei isolated with MCF were stripped of the outer nuclear membrane, had better structural integrity, including largely intact inner nuclear membrane, and less contamination from the other cell components, than those isolated with HCF. The latter had irregular surfaces and breaks in the inner nuclear membranes and more contamination with cytoplasmic debris.

Though actin is a predominantly cytoskeletal protein, it also functions as a carrier of proteins for gene expression, shuttling between cytoplasm and nuclei [Vartainen et al., Science 316 (2007) 1749-1752]. Without wishing to be bound by theory, this suggests that the actin detected by Western blots in the isolated nuclei obtained with collagenase perfusion is not necessarily due to cytoplasmic contamination. For example, it is possible that the collagenase degraded the surface of the nuclei, liberating this form of actin which then stuck to the nuclei during centrifugation. However, in this case it is likely that cytoplasmic actin also would have stuck to the nuclei. In this regard, it is noteworthy that the nuclear localization of actin by IHC occurred only in the liver sections not subjected to antigen retrieval. This indicates that the high, moist heat involved both in preparing the isolated nuclei for Western blotting and during antigen retrieval in the IHC of liver sections inhibited recognition of the nuclear actin. If this be so, then the actin bands appearing in the Western blots of nuclei isolated with collagenase perfusion were of cytoplasmic, not nuclear, origin.

The use of collagenase increased the RNA in the isolated nuclei, and this effect was exacerbated with HCF. The RNA content of isolated nuclei has been attributed to contamination with cytoplasmic RNA [Blobel and Potter, Science, 154 (1966) 1662-1665.]. The results presented herein support the option of collagenase use if yield is given priority, since it can be credited with a 10-fold increase in the number of nuclei.

REFERENCES

[1] R. Maggio, P. Siekevitz, G. E. Palade, Studies on isolated nuclei. I. Isolation and chemical characterization of a nuclear fraction from guinea pig liver, J. Cell Biol. 18 (1963) 267-291.

[2] W. C. Hymer, E. L. Kuff, Isolation of nuclei from mammalian tissues through the use of Triton X-100. J. Histochem. Cytochem, 12 (1964) 359-363.

[3] G. Blobel, V. R. Potter, Nuclei from rat liver: Isolation method that combines purity with high yield, Science, 154 (1966) 1662-1665.

[4] W. Wray, Parallel isolation procedures for metaphase chromosomes, mitotic apparatus, and nuclei, Methods Enzymol. 40 (1975) 75-89.

[5] K. Bose, D. C. Allison, An improved method of preparing nuclei for absorption cytophotometry, J. Histochem. Cytochem. 33 (1985) 65-68.

[6] K. Gorski, M. Carneiro, U. Schibler, Tissue-specific in vitro transcription from the mouse albumin promoter, Cell 47 (1986) 767-776.

[7] Y. F. Ho and T. M. Guenther, Isolation of liver nuclei that retain functional trans-membrane transport, J. Pharmacol. Toxicol. Methods 38 (1997) 163-168.

[8] D. Tapalaga, G. Tiegs, S. Angermuller, NFkappaB and caspase-3 activity in apoptotic hepatocytes of galactosamine-sensitized mice treated with TNF-alpha, J. Histochem. Cytochem. 50 (2002) 1599-1609.

[9] A. N. Prusov, O. V. Zatsepina, Isolation of the chromocenter fraction from mouse liver nuclei, Biochemistry (Mosc) 67 (2002) 423-431.

[10] K. C. Richardson, L. Jarett, and E. H. Finke, Embedding in epoxy resins for ultrathin sectioning in electron microscopy. Stain Technol 35 (1960) 313-23.

[11] W. D. Ball, and R. S. Redman, Two independently regulated secretory systems within the acini of the submandibular gland of the perinatal rat. Eur J Cell Biol 33 (1984) 112-22.

[12] E. S. Reynolds, The use of lead citrate at high pH as an electron-opaque stain in electron microscopy. J Cell Biol 17 (1963) 208-12.

What is claimed is:

1. A method for isolation of nuclei having their nuclear outer membranes cleanly removed and their nuclear inner membranes substantially intact, comprising:
    (a) providing a sample of mammalian, avian or amphibian cells;
    (b) mechanically disrupting the cells in a mildly hypertonic buffer comprising about 250 mM sucrose to generate a disrupted cell sample;
    (c) centrifuging the disrupted cell sample at 500-1000×g in a microcentrifuge for 5-15 minutes to pellet insoluble materials forming a first supernatant and a first crude nuclei pellet;
    (d) separating the first supernatant from the first crude nuclei pellet;
    (e) resuspending the pellet in a highly hypertonic buffer comprising about 2 M sucrose;
    (f) centrifuging the resuspended pellet of (e) at 10,000-20,000×g in a microcentrifuge for 10-30 minutes to generate a second nuclei pellet and a second supernatant;
    (g) separating the second supernatant and isolated pellet of (f), wherein the isolated nuclei pellet contains purified nuclei which have their nuclear outer membranes cleanly removed and their nuclear inner membranes substantially intact.

2. The method of claim 1 wherein the disrupted cell sample is centrifuged at 500-700×g.

3. The method of claim 1 wherein the disrupted cell sample is centrifuged at 600×g.

4. The method of claim 3 wherein the disrupted cell sample is centrifuged for 10 minutes.

5. The method of claim 1 wherein the resuspended pellet of step (e) is centrifuged at 10,000-16,000×g.

6. The method of claim 1 wherein the resuspended pellet of step (e) is centrifuged at 14,000-16,000×g.

7. The method of claim 6 wherein the resuspended pellet of step (e) is centrifuged for 30 minutes.

8. The method of claim 1 wherein the mildly hypertonic buffer comprises about 250 mM sucrose, 5 mM $MgCl_2$, and 10 mM Tris-HCl at pH7.4-7.6.

9. The method of claim 1 wherein the mildly hypertonic buffer comprises about 250 mM sucrose in calcium and magnesium-free PBS at pH 7.4.

10. The method of claim 1 wherein the highly hypertonic buffer comprises about 2 M sucrose, 1 mM $MgCl_2$, and 10 mM Tris-HCl pH 7.4.

11. The method of claim 1 wherein the highly hypertonic medium comprises about 2 M sucrose in calcium and magnesium-free PBS.

12. The method of claim 1 wherein the disrupted cell sample is in a volume of 500 ul-1.5 ml.

13. The method of claim 1 wherein the buffers comprise less than 5 mM PMSF, less than 10 mM EDTA, less than 20 μg/ml aprotinin and/or less than 20 μg/ml leupeptin.

14. The method of claim 13 wherein the buffers comprise less than 1 mM phenylmethyl sulfonylfluoride (PMSF), less than 5 mM EDTA, less than 10 ug/ml aprotinin and/or less than 10 ug/ml leupeptin.

15. The method of claim 1 further comprising washing the first crude nuclei pellet of step (d) in isotonic buffer before step (e).

16. The method of claim 1 further comprising washing the isolated nuclei pellet of (f) in isotonic buffer.

17. The method of claim 1 wherein the sample of cells is a tissue sample.

18. The method of claim 1 wherein the sample of cells is from a cell culture or a tissue sample.

19. The method of claim 17 wherein the tissue sample is a mammalian tissue sample.

20. The method of claim 19 wherein the mammalian tissue sample is a murine, porcine, bovine, equine or primate tissue sample.

21. The method of claim 17 wherein the tissue sample is a liver tissue sample.

22. The method of claim 17 wherein the tissue sample is a needle biopsy tissue sample.

23. The method of claim 17 wherein the tissue sample is at a concentration of 0.5 g in 4 ml of the mildly hypertonic medium.

24. The method of claim 1 consisting essentially of steps (a) through (g).

25. A method for isolation of nuclei having their nuclear outer membranes cleanly removed and their nuclear inner membranes substantially intact, comprising:
    (a) providing a sample of mammalian cells;
    (b) mechanically disrupting the cellular membrane of the cells in an ice-cold mildly hypertonic buffer at pH 7.4-7.6 to generate a disrupted cell sample;
    (c) centrifuging the disrupted cell sample at 600×g in a microcentrifuge for 10 minutes at 4° C. to generate a first supernatant and a first crude nuclei pellet;
    (d) separating the first supernatant from the first pellet,
    (e) resuspending the first crude nuclei pellet in ice-cold mildly hypertonic buffer at pH 7.4-7.6,
    (f) washing the first crude nuclei pellet by centrifuging the resuspended pellet of (e) at 600×g in a microcentrifuge for 10 minutes at 4° C. to generate a second supernatant and a second crude nuclei pellet;
    (g) separating the second supernatant from the second crude nuclei pellet;
    (h) resuspending the second crude nuclei pellet in an ice-cold highly hypertonic buffer at pH 7.4-7.6;
    (i) centrifuging the resuspended pellet of (h) at 16,000×g in a microcentrifuge at 4° C. for 30 minutes to generate a third nuclei pellet and a third supernatant;
    (j) separating the third supernatant and the third nuclei pellet;
    (k) optionally resuspending the third nuclei pellet in an ice-cold isotonic or mildly hypertonic buffer at pH 7.4-7.6;
    centrifuging the resuspended third nuclei pellet of (k) at 600×g in a microcentrifuge for 3-10 minutes at 4° C. to generate a fourth supernatant and a fourth, washed nuclei pellet;
    and separating the fourth supernatant and the fourth, washed nuclei pellet;
    (l) and resuspending the third nuclei pellet or the fourth, washed nuclei pellet in an ice-cold mildly hypertonic buffer at pH7.4-7.6, and
    freezing the resuspended pellet at −60° C. to −80° C.,
        wherein the mildly hypertonic buffer comprises about 250 mM sucrose, and the highly hypertonic buffer comprises 2.0 M sucrose, and
        wherein the nuclei in the resuspended third or fourth nuclei pellets have their nuclear outer membranes cleanly removed and their nuclear inner membranes substantially intact.

26. The method of claim 25 consisting essentially of steps (a) through (l).

27. The method of claim 25, wherein the mildly hypertonic buffer consists essentially of 250 mM sucrose, 5 mM $MgCl_2$, 10 mM Tris-HCl at pH7.4 or consists essentially of 250 mM sucrose in calcium and magnesium-free PBS.

28. The method of claim 25, wherein the highly hypertonic buffer consists essentially of 2.0M sucrose, 1 mM $MgCl_2$, 10 mM Tris-HCl pH 7.4.

29. The method of claim 25, wherein optional step (k) is not carried out.

\* \* \* \* \*